United States Patent [19]

Pacheco et al.

[11] Patent Number: 4,761,230
[45] Date of Patent: Aug. 2, 1988

[54] SMALL VOLUME TANGENTIAL FLOW FILTRATION APPARATUS

[75] Inventors: John F. Pacheco, Billerica; Donald B. Rising, Stow, both of Mass.

[73] Assignee: Millipore Corporation, Bedford, Mass.

[21] Appl. No.: 61,846

[22] Filed: Jun. 11, 1987

[51] Int. Cl.[4] .............................................. B01C 13/00
[52] U.S. Cl. .............................. 210/321.84; 210/416.1
[58] Field of Search ........... 210/195.2, 321.84, 321.75, 210/651, 445, 416.1, 446

[56] References Cited

U.S. PATENT DOCUMENTS 3,085,687  4/1963  Erbach .............................. 210/195.2
3,788,474  1/1974  Granger et al. ........... 210/321.84 X Primary Examiner—Frank Spear
Attorney, Agent, or Firm—Andrew T. Karnakis

[57] ABSTRACT

A filter system particularly useful with small sample volumes includes first and second housing sections with a flow channel extending therebetween. A membrane filter forms one boundary of the flow channel. A pair of reservoirs, one for feed and the other for permeate collection, are integrally formed with the first housing section. A fluid communication path is established from the first section to the second section and then through means of a deformable chamber to the flow channel. The deformable chamber is adjacent to a rigid surface that is integral with one of the housing sections and in this manner is adapted to pump fluid through the system when interfacing with a pump.

24 Claims, 4 Drawing Sheets

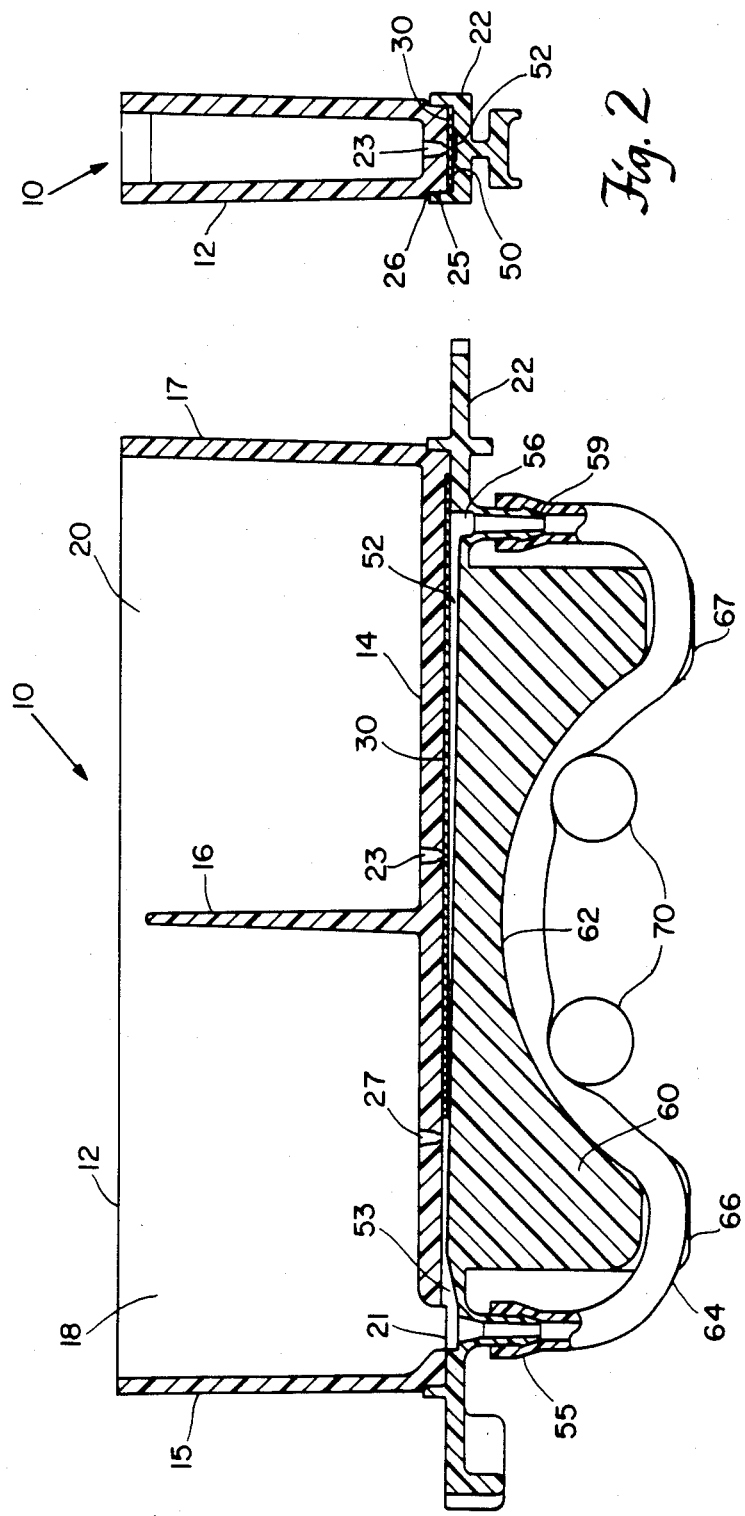

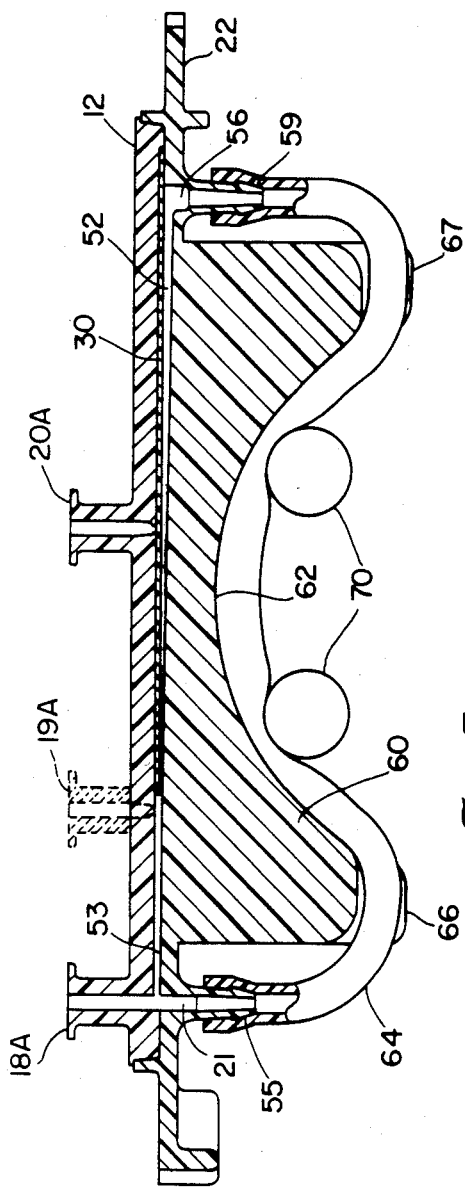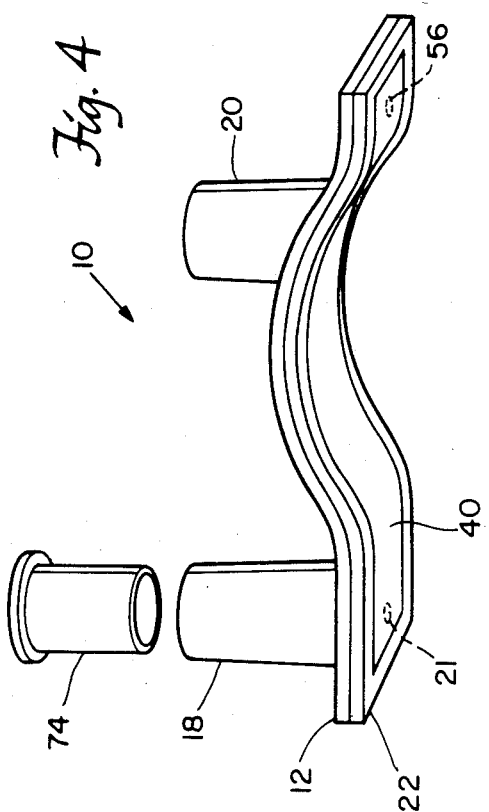

SMALL VOLUME TANGENTIAL FLOW FILTRATION APPARATUS

FIELD OF THE INVENTION

This invention relates to membrane filtration, and more particularly to the filtration of small sample volumes by use of tangential flow techniques.

BACKGROUND OF THE INVENTION

The filtration of liquid samples to either purify the sample liquid by removal of particulate or molecular contaminants or to concentrate the sample for laboratory analysis is a well developed art. Tangential flow systems are well suited for these applications because these systems generally permit higher fluxes and higher throughputs than corresponding dead-ended membrane filter systems. As used herein the term tangential flow refers to flow that is essentially parallel to the surface of a membrane filter, and a tangential flow system means a system wherein a large fraction of the liquid sample flows continuously in a direction essentially parallel to the membrane surface as opposed to a much smaller portion which flows through the membrane. Tangential flow systems can employ either microporous membranes or ultrafiltration membranes or reverse osmosis membranes whose pore sizes are such as to separate material according to molecular size. The tangential flow of liquid across the surface of the membrane continuously sweeps away the particles or molecules which the membrane has retained from the portion of the fluid stream which has passed through the membrane, thus preventing concentration polarization and/or fouling leading to improved performance in the quality of separation and flux.

Applications involving the filtration or ultrafiltration of small volume samples present difficulties, particularly when such samples contain a substantial amount of material to be retained by the membrane. As used herein small volume refers to liquid samples of 100 ml or less. Because the volumes involved are so small in these applications, the fabricated devices incorporating the membranes used to filter the sample must be small as well. Additionally, pumps and associated conduit interconnections of conventional tangential flow systems require increased priming volume which can be significant with respect to the overall volume of sample to be filtered. Therefore, although it is desirable to use tangential flow techniques for small volume filtration for the reasons given above, it is difficult to create tangential flow in these small devices. Accordingly the filtration of small sample volumes is usually accomplished through dead-ended techniques with the aforementioned inherent drawbacks of fouling and clogging.

To overcome these deficiencies, attempts have been made in the prior art to simulate tangential flow in small ultrafiltration devices. For example, stir bars have been used in certain laboratory filtration applications, but these are not effective when the sample volume is less than a few milliliters and in any event do not provide the sweeping action of tangential flow systems. It should be noted that in typical applications the sweeping velocity is zero at the center of a stir bar, and maximum at its ends. If the bar is spun fast enough to create sufficient sweeping action near its center, this can result in excessive sweeping velocity at the ends of the stir bar. This can damage the sample and cause vortexing at the center thereby entraining air in the sample.

A more recent attempt has been the use of centrifugal ultrafiltration membrane devices such as the type commercially available from Amicon Corporation as Model MPS-1. In these devices, the sample is placed in a tubular cartridge having a membrane fixedly held within the tube at an approximate 45° angle to the centrifugal force vector generated by rotation of the centrifuge. This is an attempt to create a sweeping action across the membrane surface to simulate tangential flow; however, in this device the flow is dead-ended and not truly parallel to the membrane.

Another attempt to produce tangential flow in a small filtration device is described in U.S. Pat. No. 4,343,705. That device includes two reservoirs having between them a flow channel bounded by a microporous membrane and uses gas pressure applied alternately directly upon the liquid surfaces in the reservoirs to drive the sample back and forth over the surface of the membrane. However, such an arrangement exposes the sample to contamination by the direct application of pressurized gas and requires that the residual sample volume be relatively large to prevent problems associated with the entrainment of air in the sample. Furthermore, tangential flow occurs during only a portion of the time the sample is exposed to the membrane due to the need to reverse flow direction often.

It is thus apparent that none of the above prior art attempts produce true tangential flow in the sense that the majority of the liquid sample is passed in a parallel manner continuously over the membrane surface whereupon only a small portion passes through the membrane as purified permeate. Thus the need still exists for a membrane filtration device useful with small sample volumes which is able to create true tangential flow in correspondingly small membrane devices.

SUMMARY OF THE INVENTION

The present invention overcomes the foregoing disadvantages and limitations associated with prior art membrane filtration devices by providing a self contained, tangential flow membrane filtration system. In accordance with the preferred embodiment, the system is made up of two housing sections and includes feed and permeate reservoirs which are integral with one of the sections. A flow channel extends between the two housing sections and is bounded on one side by a membrane filter adjacent to the feed and permeate reservoirs. Fluid transfer from the feed to the permeate reservoir occurs through the membrane. Tangential flow is created through a deformable pump chamber whose corresponding reaction surface is integral with the housing of the filtration device. The overall structure of the filtration device is arranged such that the device is capable of sustaining tangential flow.

Further in accordance with the preferred embodiment, the membrane filter device incorporates an ultrafiltration (UF) membrane and is used with sample liquid whose volume is 100 ml or less. The filter device includes a housing having first and second sections with a flow channel extending between these two sections. A UF membrane filter is sealed to one housing section parallel to the flow channel. The first housing section also includes separate reservoirs: an inlet or feed reservoir adapted to receive a liquid to be separated, and an outlet or permeate reservoir for collecting purified permeate or diluent when the device is used as a concentrator. A pumping chamber, which comprises a length of deformable plastic tubing, extends from an outlet in the second housing section which is in fluid communication with the feed reservoir and terminates at an inlet which is in fluid communication with the flow channel. This arrangement thus provides fluid communication between the inlet reservoir and the membrane through the flow channel. The pump chamber is located adjacent to a curved contour of the bottom of the second housing section which acts as a reaction surface or "pump shoe" against which the tubing is occluded during pumping. In operation, the inlet reservoir is filled with the liquid sample, the sample passes into the pumping chamber and then is made to flow past the membrane by the action of a peristaltic pump whose rollers are adapted to ride along the curved bottom of the second housing section and hence occlude the pump chamber to create the pumping action. A portion of the sample flow passes through the membrane as purified permeate, while the remainder returns to the inlet reservoir for recirculation. The restrictive effect of the flow channel creates a pressure in that channel which provides the driving force for flow through the membrane.

DESCRIPTION OF DRAWINGS

Other aspects, features and advantages of the present invention will become apparent from the following written description read in conjunction with the drawings.

FIG. 1 is a side view of a filtration device constructed in accordance with the preferred embodiment of the present invention included as part of a pumping system;

FIG. 2 is a cross-sectional end view of the embodiment of FIG. 1;

FIGS. 3 through 6 show alternate embodiments of the invention.

DESCRIPTION OF PREFERRED EMBODIMENT

Figure 5:
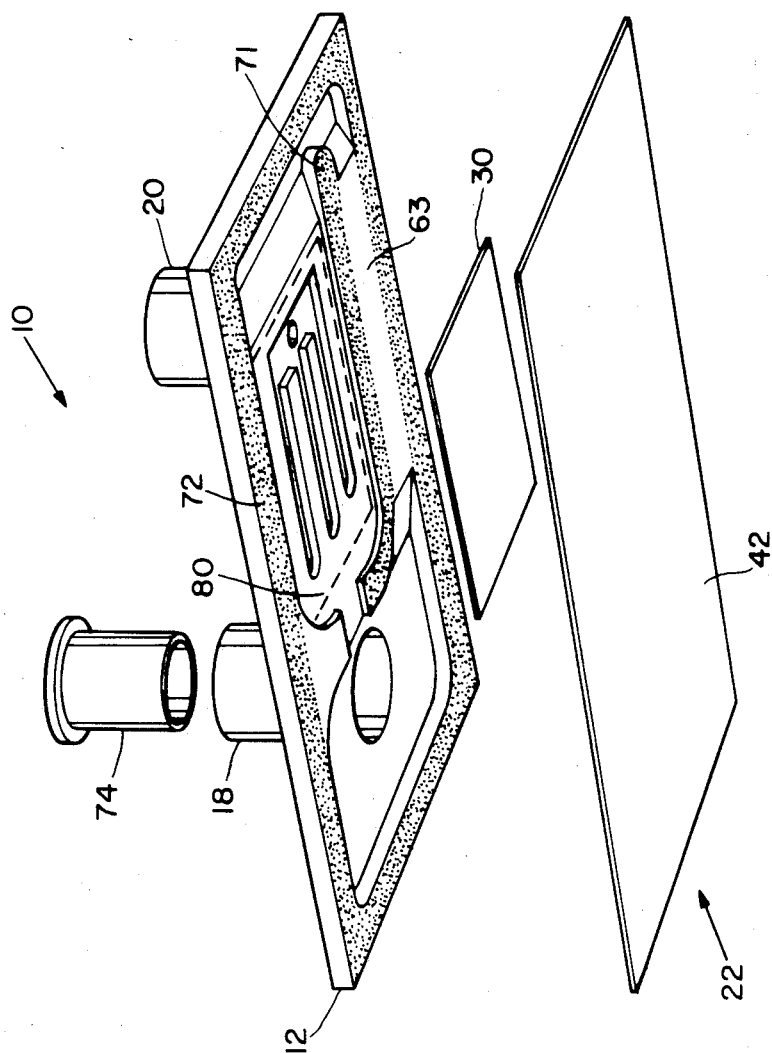

FIGS. 1 and 2 in section show a membrane filter device 10 suitable for small volume filtration which includes an upper housing 12 made of plastic material and having an elongate base 14 with a pair of liquid reservoirs extending vertically from the base as defined by transverse wall members 15, 16 and 17. The left most reservoir (as viewed in FIG. 1) serves as an inlet or feed reservoir 18 for the sample to be filtered, while the right hand reservoir is an outlet or permeate reservoir 20 for permeate collection. The filter device also includes a lower plastic housing 22 which is configured to mate with and to be sealed to the upper housing.

Between the two housings and sealingly affixed to the bottom of the upper housing 12, an ultrafiltration (UF) membrane filter 30 extends along essentially the entire length and width of the two housings. This membrane filter may be any one of a wide variety of commercially available membranes such as the type sold by Millipore Corporation under the designation PLGC. Also, although a UF membrane is described herein, a microporous or reverse osmosis membrane filter may be substituted with equally satisfactory results. A hole 21 of relatively large diameter at the bottom of the feed reservoir 18 provides fluid communication to the lower plastic housing 22 while a hole 23 in the upper housing provides fluid communication between the filtrate side of the membrane and the permeate reservoir 20. A mixing port 27 is located just beyond the downstream edge of the membrane filter to provide another fluid communication path with the feed reservoir.

Referring particularly to FIG. 2, the bottom of the upper housing 12 to which the UF membrane filter 30 is bonded forms a stepped, raised projection, 25 defining a lip 26 which extends about the entire periphery of the bottom of the housing 12. This structure facilitates the joining of the upper housing 12 to the lower housing 22 which includes a trough-like recess 50, the dimensions of which are such as to allow mating with the projection 25 (see also FIG. 1). The recess 50 includes a generally rectangular inner groove 52 that is 0.010 inches high at the inlet (i.e., furthest from the hole 21) and 0.005 inches at the outlet (i.e., closest to the hole 21). The groove is of uniform width (0.080 inches) and extends longitudinally between the housing fluid communication hole 21 and another hole 56 in the lower housing 22. Thus, the groove forms a flow channel of defined width and height which is tapered to be smaller at the outlet than at the inlet. For sake of clarity, the extent of taper of the flow channel has been exaggerated in FIG. 1.

The hole 21 extends from the housing 22 and terminates at a conduit terminal 55. A conduit terminal 59 for the hole 56 at the end of the flow channel groove 52 is similarly located on the opposite end of the lower housing 22. An arcuate-shaped support member 60 extends from the bottom of the lower housing and spans almost the entire length between the conduit terminals 55, 59. A deformable plastic tube 64 is connected to each of the conduit terminals to form a fluid-tight path and lies in the vicinity of the curved bottom surface 62 of the support member 60. The tube acts as a pumping chamber for the liquid sample and is held in position near the bottom surface 62 by means of a pair of detent grooves 66, 67 located at each end of the support member 60. As will be explained presently, this curved surface which is integral with the lower housing 22 is a reaction surface for the pump chamber tube to control the amount of occlusion and to create the pumping action for the filtration system.

As is apparent, the above structure defines a fluid communication path between the feed and permeate reservoirs 18, 20 as follows. Sample liquid placed in the feed reservoir flows through the hole 21 to the pumping chamber tube 64. From there the fluid path continues through the hole 56 to the flow channel 52 which is directly adjacent to the surface of the membrane filter 30. That portion of the sample liquid passing through the membrane filter (the filtrate) communicates with the hole 23 and eventually the permeate reservoir. The remainder of the sample liquid not passing through the membrane filter (the retentate) continues flowing along the channel 52 and returns to the bottom of the feed reservoir through a channel outlet 53 adjacent the hole 21.

To promote mixing of feed and retentate, the port 27 is located in a high velocity region of the portion of the flow channel 52 carrying retentate. This region (just beyond the edge of the membrane filter 30) has an enlarged cross-sectional area which creates a low pressure zone that allows feed to be drawn from the feed reservoir 18 into the retentate stream through the port 27. Of course, it will be apparent that with slight modifications, most notably by restricting or reducing the cross-sectional area in the vicinity of the port, it will be possible to also promote mixing by reversing the flow and hence bleeding some or all of the retentate into the feed reservoir through the port 27.

In operation as a filtering device in the batch mode, a liquid sample is supplied to the feed reservoir 18 which may then be covered by a suitable cap (not shown). The liquid flows down the reservoir through the hole 21 to partially fill the pump chamber tube 64. After the liquid sample has been loaded, the filter device 10 is positioned in a holder (not shown) which interfaces with a peristaltic pump, the rollers 70 of which are shown in FIG. 1. The rollers are aligned with the filter device such that they strike an arc adjacent the curved surface 62 of the lower housing 22. The tube is pinched against the surface 62 by the rollers and the resultant occlusion of the tube creates a pumping force to push the sample through the pumping chamber. The liquid sample then flows through the hole 56 to the flow channel 52.

As is apparent to those of skill in the art, the combination of the rapid movement of the rollers to create flow along an elongate, narrow flow path produces a sufficient back pressure to drive fluid through the membrane filter 30. The purified permeate fluid from the membrane filter passes through the hole 23 and collects in the permeate reservoir 20. The retentate, mixed with feed drawn in through the mixing port 27, returns to the feed reservoir by way of the channel outlet 53. It should be noted that an important advantage of this embodiment is that filtration pressurization is accomplished without the need of added components such as pistons and other similar pressure generators. Furthermore, the use of a tapered flow channel modifies the filtration pressure along the length of the membrane and thus makes the flow rate through the membrane filter more uniform along the entire length of the membrane in the direction of flow.

When operating in a continuous recirculation mode during concentration of batch samples, aeration problems can occur should the feed reservoir 18 run dry. This may be alleviated by making the collection volume of the permeate reservoir 20 smaller than that of the feed reservoir and thus allowing some of the collected permeate to be reintroduced into the feed reservoir. In this embodiment, this feature is accomplished by locating the permeate reservoir directly adjacent to the feed reservoir and reducing the height of the wall member 16 to allow permeate to overflow into the feed reservoir.

As illustrated in FIG. 2, the width profile of the filter device 10 is relatively narrow. This compactness permits a number of filter devices to be placed side by side such that several devices can interface with a single set of elongate peristaltic pump rollers. In this manner several samples can be processed simultaneously while having the ability to be started and stopped independently. Of course, it is equally possible if desired to provide a separate set of rollers for each device.

ALTERNATE EMBODIMENTS

FIGS. 3 through 6 illustrate alternate embodiments of the present invention wherein like numerals are used to represent the same components as those described with reference to the description of the preferred embodiment.

Although particularly useful with applications requiring integral feed and permeate reservoirs, the invention is not intended to be so limited, as may be gathered from the description of the embodiment of FIG. 3. In this alternate embodiment the relatively large volume reservoirs 18, 20 have been replaced by fittings 18A, 20A. This allows the filter device to be directly injected with sample through a syringe or to be connected to separate, remotely located reservoirs or to a process stream permitting a continuous supply of feed liquid and removal of permeate.

Focusing on the continuous feed of sample and removal of permeate, the basic configuration of FIG. 3 can serve several different applications with only slight modifications as described below:

(1) In FIG. 3, with only the fittings 18A and 20A incorporated (note the dashed lines denoting the "phantom" effect of fitting 19A), the fitting 18A is connected to a feed supply source and serves as a feed port. The fitting 20A is the permeate port which may be connected to a monitoring device, and the retentate is completely recirculated within the filter device. Such a device would be useful only where the concentration of the retained material is low.

(2) In applications where the retentate contains the material of interest, the feed port may be connected to a source of diluent and the filter device would then operate in a diafiltration mode. In this instance, the permeate could be connected to waste.

(3) It is also possible to incorporate in the device of FIG. 3 fitting 19A which serves as a retentate port. To avoid build up of the concentration of the retentate, a portion of the retentate is bled from the port 19A but otherwise the operation of this device is the same as described in (1) above. This configuration permits operation at low feed supply rates.

(4) In a variation of the device represented in (3) above, the return channel is completely blocked between fittings 18A and 19A thereby forcing all of the retentate to exit at port 19A. This would produce single-pass operation which, for effective tangential flow filtration, requires relatively high feed supply flow rates.

It should be noted that in all other respects, the operation of the variations of this embodiment are the same as that of the FIG. 1 embodiment.

FIG. 4 shows another embodiment where the upper and lower housings 12, 22 are both curved to reduce the bulkiness of the device. As with the preferred embodiment, the membrane filter (not shown) is sandwiched between these two housings and adjacent to the flow channel formed in the lower housing. In this embodiment, a flexible film 40 is sealed to the perimeter of the bottom of the lower housing 22. Liquid sample is introduced into the feed reservoir 18 and collects underneath the film which thus serves as a pumping chamber. In addition, a spring loaded piston 74 is inserted into the feed reservoir to create a positive system pressure to drive the sample liquid through the membrane filter. When sample liquid is loaded into the device and the piston is actuated, the unrestrained portion of the film 40 bulges with the filled liquid. When the film is put in contact with a pump (e.g., a peristaltic pump roller), the sample begins to flow and the operation of the device 10 of this embodiment is the same as described with respect to the preferred embodiment.

FIG. 5 shows another possible embodiment wherein the upper housing 12 includes integral feed and permeate reservoirs 18, 20 as before; however, the lower housing 22 is a deformable, flexible film 42. The underside of the upper housing includes a pair of elongated spacers 71, 72 extending longitudinally in the vicinity of the feed and permeate reservoirs. The membrane filter 30 is bonded to the upper housing between the two spacers. In operation, a rigid backing plate (not shown) aligns with and covers and restrains film 42 in the membrane filter/spacer region to create a flow channel 80 of defined width and height. Once again the piston 74 enhances system operation to create a positive pressure for filtration. External rollers (not shown) are aligned to contact the unrestrained portion of the film which is bulged by the action of the piston and serves as a pumping chamber in the region 63. The rollers squeeze the "inflated" film against the upper housing to produce tangential flow in the channel. The permeate then flows through the membrane filter and collects in the permeate reservoir.

Figure 6:
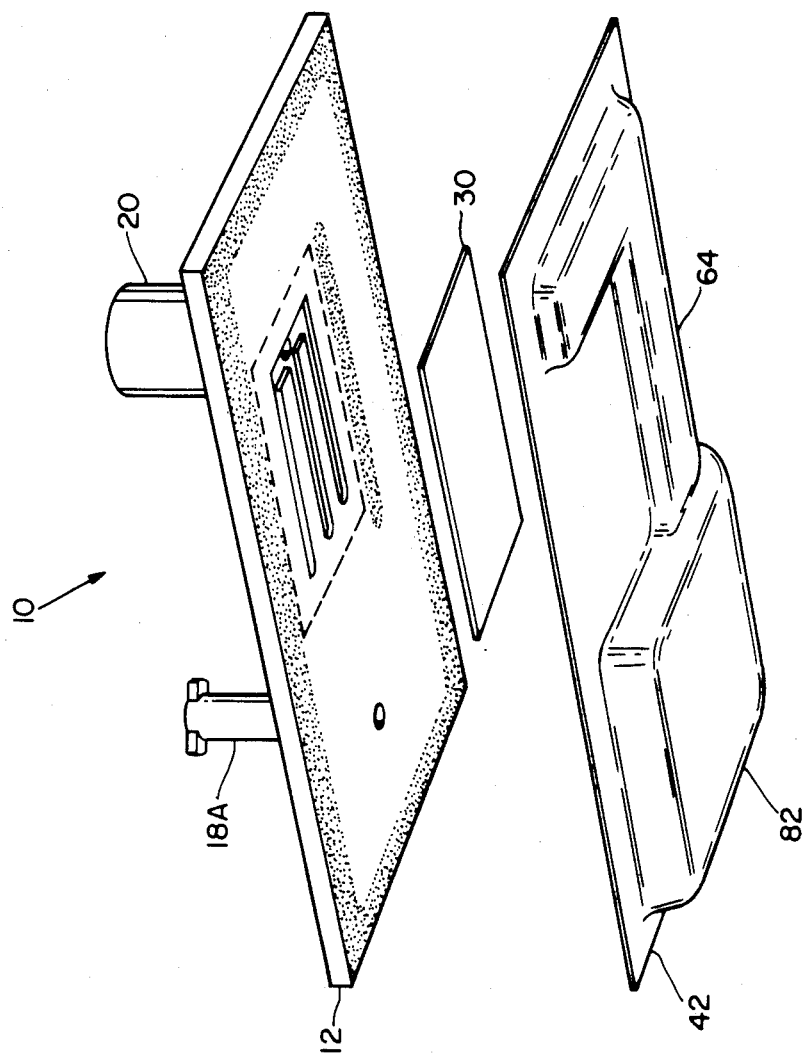

FIG. 6 shows another embodiment which is a variation of the embodiment of FIG. 5. In this instance, the construction and operation is identical to the device of FIG. 5 except that the film 42 which forms the lower housing is bulged to form a pouch 82 and a pumping chamber 64 and the feed reservoir 18 is replaced by a fitting 18A. The pouch serves as the reservoir for the sample liquid prior to filtration/concentration processing and is filled through the fitting 18A which is then capped. To generate system pressure for filtration, the pouch is gently squeezed in any suitable manner while the rollers (not shown) of a peristaltic pump bear on the pumping chamber portion of the film to create the necessary flow.

Although several embodiments of the invention have been described in detail above, modifications will become apparent to those of skill in the art. For example, it is also possible, whether operating in a batch or continuous mode, to add diluent to the feed such that the filter device accomplishes fluid purification by diafiltration. Still further, the flow channel can be altered such that it is of uniform height and width along most of its length with a restriction formed near the outlet. This configuration would produce an even more uniform flow rate through the membrane along its entire length. A roller-type peristaltic pump has been described throughout as the preferred pumping mechanism; however, any suitable pump such as a finger-type pump could be used.

Accordingly, the invention is only intended to be limited by the appended claims.

We claim:

1. A filtration system particularly useful with small sample volumes comprising:
    a housing having first and second sections;
    a flow channel extending longitudinally between at least a portion of said first and second sections;
    a membrane filter positioned between said first and second sections and forming one boundary of said flow channel;
    means for supplying sample fluid to said first section and being in fluid communication with said second section;
    fluid transfer means in fluid communication with said supply means and said flow channel;
    said fluid transfer means including deformable chamber means adapted to hold and pump a volume of fluid therethrough and a rigid surface adjacent said chamber means for controlling the extent of deformation when fluid is pumped through said chamber means, said rigid surface being integral with one of said sections.

2. The apparatus of claim 1 wherein said supply means includes first reservoir means integral with said first section and further comprising second reservoir means integral with said first section and being in fluid communication with the filtrate side of said membrane filter.

3. The apparatus of claim 1 wherein said flow channel includes means to modify the flow rate through said membrane filter along the length thereof.

4. The apparatus of claim 3 wherein said flow rate modification means comprises a tapered flow channel at least one of whose dimensions at the outlet are smaller than at the inlet.

5. The apparatus of claim 1 wherein said membrane filter is sealed to one of said sections.

6. The apparatus of claim 1 wherein said deformable chamber means is a flexible tube.

7. The apparatus of claim 6 wherein said rigid surface is a curved contour of said second section and said tube is held in position adjacent said curved contour.

8. The apparatus of claim 1 wherein said deformable chamber means is a deformable film.

9. The apparatus of claim 8 wherein said film is formed as a pouch.

10. The apparatus of claim 2 wherein said first reservoir means is a feed reservoir for receiving the sample to be filtered and said second reservoir means is a permeate reservoir, and including means for allowing excess permeate to flow back into said feed reservoir.

11. The apparatus of claim 10 wherein said feed and permeate reservoirs are directly adjacent to one another and separated by a wall member, the height of which is reduced to allow excess permeate to overflow back into said feed reservoir.

12. The apparatus of claim 1 wherein said second housing section is a deformable film.

13. The apparatus of claim 1 wherein said supply means is comprised of a fitting and includes a second fitting for removal of permeate.

14. The apparatus of claim 13 including a third fitting for removal of retentate.

15. The apparatus of claim 1 wherein said membrane filter is a microporous filter.

16. The apparatus of claim 1 wherein said membrane filter is an ultrafilter.

17. The apparatus of claim 1 wherein said membrane filter is a reverse osmosis membrane.

18. The apparatus of claim 13 including means for prohibiting return of retentate to the supply means.

19. The apparatus of claim 8 wherein said film is inflated by internal pressure created by a piston.

20. The apparatus of claim 8 wherein said film is inflated by internal pressure created by sealing said supply means and applying external pressure on a portion of the film.

21. The apparatus of claim 1 including pumping means cooperating with said fluid transfer means.

22. The apparatus of claim 21 wherein said pumping means is a roller peristaltic pump, the rollers of which contact said deformable chamber means.

23. The apparatus of claim 2 including feed reservoir mixing means.

24. The apparatus of claim 23 wherein said mixing means comprises a port in said first reservoir communicating with said flow channel.

* * * * *